United States Patent [19]
Bergstra et al.

[11] Patent Number: 5,362,411
[45] Date of Patent: Nov. 8, 1994

[54] ANTIRUST/DISPERSANT ADDITIVE FOR LUBRICANTS

[75] Inventors: Raymond Bergstra, Mt. Laurel; Andreas Logothetis, Collingswood; William F. Olszewski, Cherry Hill, all of N.J.; Shi-Ming Wu, Newtown, Pa.

[73] Assignee: Mobil Oil Corporation, Fairfax, Va.

[21] Appl. No.: 59,150

[22] Filed: May 10, 1993

[51] Int. Cl.$^5$ ............... C10M 133/16; C10M 133/44; C07D 249/16; C07D 403/00
[52] U.S. Cl. ................... 252/51.5 A; 252/49; 252/49.6; 548/257; 548/260
[58] Field of Search .................. 252/51.5 A, 49, 49.6; 548/257, 260

[56] References Cited

U.S. PATENT DOCUMENTS

| | | | |
|---|---|---|---|
| 3,788,993 | 1/1974 | Andress | 252/51.5 A |
| 4,963,278 | 10/1990 | Blain et al. | 252/51.5 A |
| 5,049,293 | 9/1991 | Blain et al. | 252/49.6 |

*Primary Examiner*—Prince Willis, Jr.
*Assistant Examiner*—Cephia D. Toomer
*Attorney, Agent, or Firm*—Alexander J. McKillop; Malcolm D. Keen; Charles A. Malone

[57] ABSTRACT

Reaction products of hydrocarbylsuccinic anhydrides, polyamines and triazoles, as exemplified by XRT 2143A, have been found to be effective rust/corrosion inhibiting, thermal stabilizing and superior dispersant additives with excellent cleanliness feature for fuels and lubricants. Enhanced antioxidancy is also observed upon boration of these reaction products.

19 Claims, No Drawings

ANTIRUST/DISPERSANT ADDITIVE FOR LUBRICANTS

BACKGROUND OF THE INVENTION

1. Field of the Invention

This application is directed to novel antirust/dispersant additives for lubricants comprising reaction products of hydrocarbyl succinic anhydrides, polyamines and triazoles.

2. Description of Related Art

Alkenylsuccinic anhydrides have been widely used in petroleum and synthetic lubricant products for their lubricity and solvency. Products made by reacting amines with alkyl or alkenylsuccinic anhydrides to form alkyl or alkenylsuccinimides are well known as detergents and dispersants for lubricants and fuels. Post-reaction of these succinimides to introduce other beneficial functional groups can be performed.

Triazoles such as benzotriazole can be used as metal corrosion inhibiting antirust agents. See U.S. Pat. No. 3,413,227. Also, U.S. Pat. No. 4,859,352 discloses the use of sulfur-free triazole derivatives as a metal deactivator.

U.S. Pat. Nos. 5,185,090; 5,068,045 and 7,599,183 for example describe the use of borated adducts in various lubricants and fuels and are incorporated herein by reference.

It has been found that lubricant compositions containing small additive concentrations of reaction products derived from hydrocarbyl succinic anhydrides, polyamines and triazoles possess excellent rust/corrosion inhibiting, thermal stabilizing and cleanliness as well as excellent dispersancy properties for fuels and lubricants. Furthermore, the borated version of these additives can enhance the antioxidant performance.

BRIEF SUMMARY OF THE INVENTION

The present invention is directed to lubricant compositions containing additive amounts of reaction products of triazoles, amines and hydrocarbyl anhydrides. More specifically the present invention is directed to such compositions containing a major amount of an oil of lubricating viscosity and a minor additive amount of the reaction product of a hydrocarbon succinic anhydride, a polyamine and a triazole, to the reaction products per se and to the use of such reaction products in lubricants and fuels and further to post reacted borated products of these.

It is therefore an object of this invention to provide improved lubricant compositions, novel additive reaction products and the use thereof in oleaginous fluids, greases and improved fuel compositions.

DESCRIPTION OF THE PREFERRED EMBODIMENTS

The products of reaction described herein may be advantageously made as set forth below:

Hydrocarbylsuccinic anhydrides (I) can have the following structural formula:

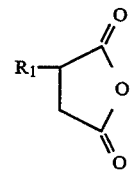

Where $R_1$ is hydrocarbyl, preferably an alkyl or alkenyl or polyolefin group having 1 to 100,000 carbon atoms, preferably 20 to 10,000 carbon atoms and more preferably 40 to 300 carbon atoms. The polyamines can contain any primary or secondary amine and combinations thereof. Any appropriate triazoles (II) may be used herein, where $R_2$ is hydrogen or an alkyl, aryl, arylakyl, alkylaryl or carboxy group of 1 to 50 carbon atoms. A preferred triazole is tolyltriazole.

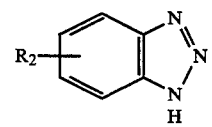

Hydrocarbyl as used herein includes but is not limited to alkyl, aryl, alkylaryl, arylalkyl, alkenyl, cycloalkyl or cycolalkenyl groups containing from 8 to about 30 carbon atoms, preferred are 10 to 22 carbon atoms. Preferably, hydrocarbyl is an alkyl or aryl, or alkylaryl group. Suitable amines include any such hydrocarbyl amine, e.g., polyethylene amines, polypropylene amines, primary or secondary, straight and branched chain amines and alkenyl succinimides.

$C_1$ to about $C_{400}$ alkenyl succinic anhydrides having a molecular weight of from about 400 to about 5,000 are suitable for use herein as well as their corresponding acids. Preferred are such succinic anhydrides as polyisobutenyl succinic anhydride.

The molar ratio of the various reactants may vary from 2/2/3 to 100/10/1 and preferably 4/2/1 to 5/1/1 of anhydride/polyamine/triazole. In the initial reaction the temperature between hydrocarbylsuccinic anhydrides and polyamines is kept at temperatures less than 85° C. to minimize the formation of condensation, succinimide, preferably the temperature is maintained from about 50° C. to 80° C. at ambient pressure, although higher pressure of up to about 100 psi may be used if thought desirous. When a solvent is thought desirable, a suitable hydrocarbon solvent such as toluene, xylene and other aliphatic alkanes may be used.

The reaction conditions, however, are dependent upon the specific reactants used. For instance, by mixing condensation hydrocarbylsuccinimides and triazoles under elevating temperatures up to about 250° C. having goof antioxidant/antirust/dispersant lubricants, additives where the hydrocarbylsuccinimides are the condensation product of hydrocarbylsuccinic anhydrides and/or acid equivalents with polyamines and/or primary amines.

Borated products may be produced by any means known in the art. Alkyl or metaborates as well as boric acid are highly suitable borating agents. As noted hereinabove the borated products enhance the antioxidant characteristics of the additive reaction products.

The additives in accordance with the invention have the ability to improve the rust/corrosion inhibiting, thermal stabilizing and dispersant and cleanliness and antioxidant characteristics of various oleaginous materials such as hydrocarbyl lubricating media, which may comprise liquid oils in the form of either a mineral oil or a synthetic oil, or in the form of a grease in which the aforementioned oils are employed as a vehicle, or liquid hydrocarbyl fuels.

The additives embodied herein are utilized in lubricating oil or grease compositions in an amount which imparts the aforementioned characteristics to the oil or grease as well as reducing the friction of engines operating with the oil in its crankcase. Concentrations of about 0.001 to about 15 wt. % based on the total weight of the composition can be used. Preferably, the concentration is from 0.1 to about 3 wt. %. It is expected that these materials would also be suitable for use in liquid hydrocarbyl or hydrocarboxy, oxygenated or alcoholic or mixed hydrocarbyl/alcoholic or oxygenated fuel compositions as well as diesel fuels and fuel oils such as heating oils. They are utilized in fuels in amounts of from about 25 to 500 pounds of additive per thousand barrels of fuel and preferably from about 50 to about 250 pounds per 1000 barrels of fuel.

It is to be understood, however, that the compositions contemplated herein can also contain other materials. For example, corrosion inhibitors, extreme pressure agents and the like can be used as exemplified respectively by metallic phenates sulfonates, polymeric succinimides, non-metallic or metallic phosphorodithioates and the like. These materials do not detract from the value of the compositions of this invention, rather the materials enhance the beneficial characteristics of the disclosed additive products in accordance with the invention.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The following examples are merely illustrative and are not meant to be limitations on the scope of this invention.

EXAMPLE 1

A one liter, four-neck flask was equipped with thermometer, condenser, agitator and $N_2$ sparger. Approximately 190 g(0.134 mol) of polyisobutenylsuccinic anhydride (PIBSA), 100 ml of toluene and 13.3 g(0.07 mol) of tetraethylenepentamine (TEPA) were charged to the reactor and heated to 80° C. for two hours. Tolyltriazole (13.3 g, 0.10 mol) was then added to the mixture and further reacted for three hours at reflux. The resulting mixture was filtered and evaporated under reduced pressure at 130° C. to yield 215 g of viscous brown fluid.

EXAMPLE 2

The same reaction conditions as described in Example 1 were followed with one modification; the final reaction mixture was further reacted with 62 g (1.0 mol) of boric acid.

EXAMPLE 3

The same reaction conditions as described in Example 1 were followed with two exceptions: approximately 280 g of polyisobutenylsuccinic anhydride was used and at the last step of the reaction, a mixture of tolyltriazole (13.3 g) and boric acid (62 g) was introduced together.

EXAMPLE 4

Approximately 194 g (0.067 mol) of polyisobutenylsuccinimide (the condensated reaction product of PIBSA+TEPA) and 6.7 g (0.050 mol) of tolyltriazole were heated to 150° C. for four hours under nitrogen.

EVALUATION OF PRODUCTS

One percent (1%) each of Examples 1–3 was blended into a solvent refined mineral oil and evaluated for its antioxidation characteristics.

TABLE 1

| Viscosity Item | Catalytic Oxidation Test 325° F., 40 Hours | | |
|---|---|---|---|
| | % Change in KV. % | Acid Number Sludge | % Change in TAN |
| Base Oil (200 second, | 174.5 | Heavy | 20.08 |

TABLE 1-continued

| | Catalytic Oxidation Test 325° F., 40 Hours | | |
|---|---|---|---|
| Viscosity Item | % Change in KV. % | Acid Number Sludge | % Change in TAN |
| solvent refined, paraffinic neutral mineral oil) | | | |
| 1% of Example 1 in above oil | 270.3 | Light | 18.11 |
| 1% of Example 2 in above oil | 56.1 | Moderate | 2.91 |
| 1% of Example 3 in above oil | 45.4 | Moderate | 3.44 |

The Catalytic Oxidation results confirm the good control in the viscosity and acidity increase. These additives demonstrate moderate antioxidant properties at only 1% concentration level.

The Catalytic Oxidation Test may be summarized as follows: Basically the lubricant is subjected to a stream of air which is bubbled through the oil formulation at the rate of five liters per hour at 325° F. for 40 hours. Present in the composition are samples of metals commonly used in engine construction, namely iron, copper, aluminum and lead, see U.S. Pat. No. 3,682,980 incorporated herein by reference for further details.

One and one half percent of Examples 1 and 4 were blended into an oil formulated without antirust and dispersant additives and evaluated for cleanliness.

TABLE 2

| | API PG-2 Data and Specifications | | | |
|---|---|---|---|---|
| | | | PG-2 Cleanliness | |
| Formulation | L-33 | L-60 | Sludge | Varnish/Carbon |
| 1.5% of Example 1 in formulated oil without antirust and dispersant additives | Pass | Pass | 9.75 | 9.50 |
| 1.5% of Example 4 in formulated oil without antirust and dispersant additives | Pass | Pass | 9.70 | 8.90 |
| Specification | Pass | Pass | >9.50 | >8.0 |

In the L-33 Moisture Corrosion Test, Dana Model 30 hybrid rear axle assembly is used in a test specifically designed to evaluate corrosion resistance characteristics of gear lubricants. The lubricant capacity is 1.2 L (2½ pints). In order to run the test 29.6 cm<3> (one ounce) of distilled water is added to the lubricant to increase the severity of the test. The unit is monitored at 2500 rpm for four hours at 82° C. (180° F.) lubricant temperature. After the monitoring period, the assembly is stored for seven days at a temperature of 52° C. (125° F.). Following storage, the unit is disassembled and the cover plate, differential case, gear teeth and bearings are inspected for rust. In order to receive a "pass" in the L-33 Moisture Corrosion Test, no rust is allowed on the gear teeth, bearings or any other functioning part of the rear axle assembly. It should be noted that the cover of the rear axle assembly is more susceptible to rust, and therefore may have no more than 1% of the surface rusted in order to receive a "pass" rating in accordance with the L-33 Moisture Corrosion Test. Accordingly, if there is rust on any of the functioning parts of the rear axle assembly or if there is rust on more than 1% of the surface of the cover, a "fail" rating is received. The L-33 Moisture Corrosion Test is part of the MII-L-2105C specification for gear lubricants, and is recognized worldwide as a standard for rust performance.

The L-60 Thermal Oxidation Stability Test is performed on a lubricant in a heated gear box. L-60 is currently being approved as a standard lubricant testing method by ASTM. The proposed lubricant is tested within a heated gear box containing two spur gears and a test bearing while operating at a predetermined load with copper strip blanks within the heated gear box. For further details please see U.S. Pat. No. 5,157,963. The L-60 Test conditions were as follows: Hours run, 50; Air temperature average 163.3° C.; Test oil temperature average 162.8° C. Test oil Viscosity centistoke at 212° F. (100° C.) (ASTM D 445); new oil 25.81 after 50 hours 33.52, 28.87% increase.

The API (American Petroleum Institute) PG-2 Cleanliness Test may be briefly described as follows: A system for rating gear cleanliness on both large and small spur gears of the L-60 test is determined, the current trial system uses 10=clean to 0=dirty with sludge and varnish/carbon rated separately on the front and back sides of gears.

The use of additive concentrations of reaction products in the above-mentioned compositions in premium quality automotive engine/gear oil and marine lubricants and fuels will significantly enhance the thermal-/oxidative stability, rust/corrosion inhibition, dispersancy/detergency, and cleanliness.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

We claim:

1. An improved lubricant composition comprising a major proportion of an oil of lubricating viscosity or grease prepared therefrom, and about 0.001 to about 15 wt. % of a multifunctional rust/corrosion inhibiting, thermal stabilizing, cleanliness and dispersant additive product of reaction prepared by reacting (1) a hydrocarbyl succinic anhydride, (2) a polyamine and (3) a triazole and wherein the reaction is carried out in molar ratios of said anhydride/polyamine/triazole varying from about 2/2/3 to about 100/10/1 at temperatures varying from about 50° C. to less than about 85° C. for the initial reaction between the anhydride and the polyamine and up to about 250° C. for subsequent reactions, under autogenous pressure or pressures varying from ambient to about 100 psi with the reaction time varying from about one hour to about 48 hours sufficient to obtain the desired additive product of reaction or (4) optionally reacting said anhydride and polyamine together and thereafter reacting a mixture of said triazole and a boronating agent therewith or post reacting said anhydride/polyamine/triazole additive product with said boronating agent thereby providing a borated additive product of reaction.

2. The composition of claim 1 wherein said additive product of reaction is prepared by reacting a hydrocarbylsuccinic anhydride having the below structural formula (I), a hydrocarbyl polyamine and a triazole of the below structural formula (II):

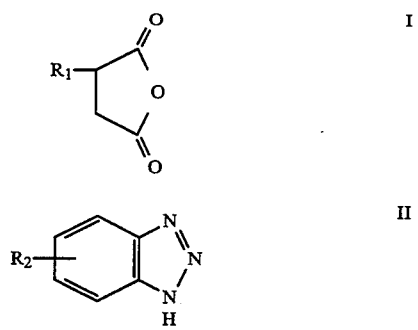

where $R_1$ is hydrocarbyl having 1 to 100,000 carbon atoms and $R_2$ is hydrogen or hydrocarbyl having 1 to 50 carbon atoms.

3. The composition of claim 1 wherein said anhydride is polyisobutenylsuccinic anhydride, said amine is tetraethylenepentamine and said triazole is tolyltriazole.

4. The composition of claim 1 wherein said anhydride is polyisobutenylsuccinic anhydride, said amine is tetraethylenepentamine, said triazole is tolyltriazole and said boronating agent is boric acid.

5. The composition of claim 1 wherein the initial reaction between said anhydride and said amine provides a polyisobutenyl-succinimide thereafter reacted with tolytrizole.

6. The lubricant composition of claim 1 wherein said oil of lubricating viscosity is selected from the group consisting of (1) mineral oils, (2) synthetic oils, (3) or mixtures of mineral and synthetic oils or is (4) a grease prepared from any one of (1), (2) or (3).

7. The composition of claim 6 wherein the lubricant contains from about 0.001 to about 10 wt. % based on the total weight of the composition of the additive product of reaction.

8. The composition of claim 6 wherein the lubricant is a mineral oil.

9. The composition of claim 6 wherein the lubricant is a synthetic oil.

10. A process of preparing a multifunctional rust/corrosion inhibiting, thermal stabilizing, cleanliness and dispersant additive product of reaction by reacting (1) a hydrocarbyl succinic anhydride, (2) a polyamine and (3) a triazole and wherein the reaction is carried out in molar ratios of said anhydride/polyamine/triazole varying from about 2/2/3 to about 100/10/1 at temperatures varying from about 50° C. to less than about 85° C. for the initial reaction between the anhydride and the polyamine and up to about 250° C. for subsequent reactions, under autogenous pressure or pressures varying from ambient to about 100 psi with the reaction time varying from about one hour to about 48 hours sufficient to obtain the desired additive product of reaction or (4) optionally reacting said anhydride and polyamine together and thereafter reacting a mixture of said triazole and a boronating agent therewith or post reacting said anhydride/polyamine/triazole additive product with said boronating agent thereby providing a borated additive product of reaction.

11. The process of claim 10 wherein said additive product is prepared from a hydrocarbylsuccinic anhydride having the below structural formula and a triazole of the below structural formula:

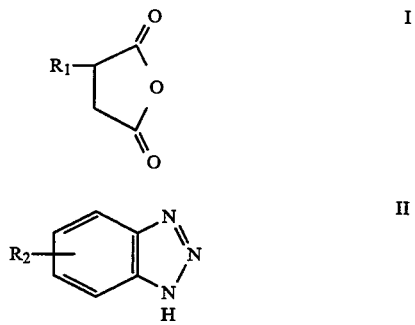

where $R_1$ is hydrocarbyl having 1 to 100,000 carbon atoms, $R_2$ is hydrogen or hydrocarbyl having 1 to 50 carbon atoms.

12. The process of claim 11 wherein the reactants are polyisobutenylsuccinic anhydride, tetraethylenepentamine and tolyltriazole.

13. The process of claim 11 wherein the reactants are polyisobutenylsuccinic anhydride, tetraethylenepentamine, tolyltriazole and boric acid.

14. A lubricant additive product of reaction prepared by reacting hydrocarbylsuccinic anhydrides, polyamines and triazoles and wherein the reaction is carried out by reacting (1) a hydrocarbyl succinic anhydride, (2) a polyamine and (3) a triazole and wherein the reaction is carried out in molar ratios of said anhydride/polyamine/triazole varying from about 2/2/3 to about 100/10/1 at temperatures varying from about 50° C. to less than about 85° C. for the initial reaction between the anhydride and the polyamine and up to about 250° C. for subsequent reactions, under autogenous pressure or pressures varying from ambient to about 100 psi with the reaction time varying from about one hour to about 48 hours sufficient to obtain the desired additive product of reaction or (4) optionally reacting said anhydride and polyamine together and thereafter reacting a mixture of said triazole and a boronating agent therewith or post reacting said anhydride/polyamine/triazole additive product with boronating agent thereby providing a borated additive product of reaction.

15. The additive of claim 14 hydrocarbylsuccinic anhydride having the below structural formula (I), hydrocarbyl polyamine and a triazole of the below structural formula (II):

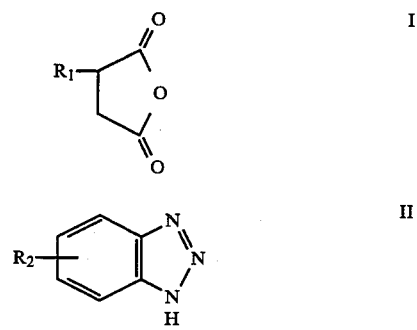

where $R_1$ is hydrocarbyl having 1 to 100,000 carbon atoms, $R_2$ is hydrogen or hydrocarbyl having 1 to 50 carbon atoms.

16. The additive of claim 14 wherein the reactants are polyisobutenylsuccinic anhydride, tetraethylenepentamine and tolyltriazole.

17. The additive of claim 14 wherein the reactants are polyisobutenylsuccinic anhydride, tetraethylenepentamine, tolyltriazole and boric acid.

18. The additive of claim 14 wherein the reactants are polyisobutenylsuccinimide and tolyltriazole.

19. A method of preparing an improved lubricant comprising adding to said lubricant a minor multifunctional corrosion inhibiting, thermal stabilizing, cleanliness and dispersant additive product of reaction from about 0.001 to about 10 wt. % based on the total weight of the lubricant composition.

* * * * *